United States Patent [19]
Corder

[11] Patent Number: 5,817,142
[45] Date of Patent: Oct. 6, 1998

[54] ELECTRICAL APPARATUS FOR KILLING MICRO-ORGANISMS IN THE HUMAN BODY

[76] Inventor: Lester J. Corder, 15400 Fielding, Detroit, Mich. 48223

[21] Appl. No.: 814,054

[22] Filed: Mar. 10, 1997

[51] Int. Cl.[6] ..................................................... A61N 1/32
[52] U.S. Cl. ............................................ 607/76; 607/145
[58] Field of Search ................................ 607/2, 76, 145, 607/150, 115

[56] References Cited

U.S. PATENT DOCUMENTS

| | | | |
|---|---|---|---|
| 3,540,453 | 11/1970 | Sugimori | 607/76 |
| 4,919,140 | 4/1990 | Borgens et al. | 607/76 |
| 5,148,772 | 9/1992 | Kirschbaum | 119/5 |
| 5,188,738 | 2/1993 | Kaali et al. | 210/748 |
| 5,326,530 | 7/1994 | Bridges | 422/22 |
| 5,393,541 | 2/1995 | Bushnell et al. | 426/237 |

OTHER PUBLICATIONS

"A Cure for All Diseases" by Hulda Regehr Clark, Ph.D, Aug. 1995.

*Primary Examiner*—William E. Kamm
*Assistant Examiner*—Kennedy J. Schaetzle
*Attorney, Agent, or Firm*—Charles W. Chandler

[57] ABSTRACT

An electrical oscillator circuit delivers high frequency oscillating current to a pair of hand-held electrodes for the purpose of killing harmful viruses, parasites and micro-organisms in the person's body. In a preferred form of the invention, the oscillator circuit is powered by a D.C. power source that includes a conventional one hundred twenty volt A.C. outlet and an A.C.-D.C. convertor plugged into the outlet.

The device could also be solar powered.

1 Claim, 2 Drawing Sheets

5,817,142

ELECTRICAL APPARATUS FOR KILLING MICRO-ORGANISMS IN THE HUMAN BODY

BACKGROUND OF THE INVENTION

This invention relates to an electrical apparatus designed to kill bacteria, viruses, toxins, and micro-organisms in a human undergoing treatment. In a preferred form, the invention comprises a D.C. voltage source that comprises a conventional 120 volt A.C. outlet, and an A.C.-D.C. convertor receivable into the outlet. An electrical oscillator is powered by the D.C. voltage source to deliver high frequency oscillating current to two portable electrodes.

The person holds the electrodes in his or her hands for a predetermined treatment period, during which time the high frequency current passes through the electrodes into the person's body for killing or destroying harmful micro-organisms in the person's body. A normal treatment cycle is three treatments with a twenty to thirty minute break off the machine between each seven to ten minute treatment. A good practice is one treatment a day for a one week period; then one treatment a week thereafter for maintenance to achieve a desirable effect. The electrodes are connected to the oscillator, so as to be alternately exposed to positive peaks in the oscillating current. One electrode will be in a circuit with a positive peak while the other electrode is in a circuit with a negative peak, and vice versa.

Prior to the present invention, various electrical circuits and devices have been devised for the purpose of killing bacteria and micro-organisms.

U.S. Pat. No. 5,393,541, issued to A. Bushnell et al on Feb. 28, 1995, discloses an apparatus for killing microorganisms in food products, particularly liquid or semi-liquid food products such as milk, yogurt, orange juice, and tomato soup. The apparatus comprises two electrodes in contact with the food product, and an electric power source for supplying power to one of the electrodes, whereby current flows through the food product and kills bacteria and micro-organisms having a potential harmful effect on food product quality.

The patentee contemplates pulsed current flows on the order of 20,000 amps, and pulse duration periods on the order of two microseconds. The patent teaches systems for periodically reversing the current flow to prevent polarization effects that can cause an agglomeration of food product on the anode electrode (i.e. the electron collection electrode)

The patent references earlier patents that deal with the bactericidal effects of electrical currents for treating food products.

U.S. Pat. No. 5,326,530, granted to J. E. Bridges on Jul. 5, 1994, relates to an electric apparatus for killing noxious biological organisms in contaminated materials, e.g. foods, pharmaceuticals and hospital wastes. The material to be treated is passed through a chamber that comprises two electrodes specially designed to prevent arc overs or localized current flows that can disrupt the biological killing process. The patentee contemplates the use of high energy electrical fields on the order of 3000 volts per centimeter of electrode surface area. The patentee envisions the use of pulse-type currents as a mechanism for reducing voltage build-ups that can cause current arc overs.

U.S. Pat. No. 5,148,772, granted to R. Kirshbaum on Sep. 22, 1992, relates to an electrical apparatus for killing harmful bacteria in fish aquariums. The apparatus comprises a positive electrode and a negative electrode suspended from an electrical control box to extend downwardly into the aquarium water at spaced points near opposite ends of the aquarium tank. The electrodes are supplied with low voltage D.C. current that is apparently of sufficient magnitude to kill harmful bacteria in the water. Voltages up to about 3 volts D.C., and currents up to about 10 milliamps are contemplated.

U.S. Pat. No. 5,188,738, issued to S. Kaali, discloses an electrical apparatus for treating human blood to remove (or kill) potentially harmful bacteria, virus, parasites and fungus in the blood. The apparatus includes plural electrodes in the wall of a conduit that carries the blood, whereby the flowing blood is subjected to a low voltage A.C. field. The A.C. voltage is less than twelve volts. Current flow across the electrodes is typically less than 500 microamperes. Electrodes are of sufficient length or number as to provide a treatment duration time of about three minutes. Presumably the A.C. voltage is 120 hertz, i.e. normal household voltage. The patentee indicates that the biological killing action of this low voltage A.C. current may result from the production or elimination of different ions, radicals, gases or pH levels that affect biologically active molecules or cells in the blood.

A book authored by Hulda Regehr Clark, Ph.D., entitled "The Cure For All Diseases" published in the United States by Pro Motion Publishing in San Diego, Calif. (copyright date 1995) discloses an electrical apparatus for killing viruses, bacteria, parasites, toxins, microorganisms and molds in the human body. The apparatus comprises a nine volt battery connected to an electronic circuit for supplying an oscillating current to two copper electrodes. The human patient holds the electrodes in his or her hands for a sufficient time to kill harmful parasites in the human body. In one form of the apparatus, the frequency of the voltage supplied to the electrodes is about 30 KHz. Treatment time is on the order of seven minutes. The treatments may be repeated, as necessary to achieve a desirable effect. The book mentions three treatments a day for a one week period.

The present invention is directed to an apparatus that is a variant of the human treatment systems disclosed in the above-mentioned book by H.R. Clark. In the preferred form of the present invention, the electrical power source comprises a conventional household voltage source, 120 volt A.C. An A.C.-D.C. convertor is used to supply D.C. voltage to an oscillator circuit designed to produce an oscillating voltage in the frequency range up to about 900 KHz. Preferably the oscillator comprises a variable capacitance for varying the oscillator voltage within limits, whereby the treatment system is adapted to kill, or remove, a variety of different bacteria, viruses, bacteria, toxins and harmful micro-organisms. The system comprises two hand-held electrodes connected to the oscillator output, such that oscillating current is passed through the human body for killing the harmful substances.

The system operates at voltages and current levels that are safe for human tissues and organs. A principal advantage of the system is that it uses the conventional household A.C. voltage as a power source, so that the system can be used for prolonged time periods without having to replace a battery power source. Another advantage of the A.C. voltage source is that, after conversion to a D.C. voltage, the voltage level can be higher than voltage levels obtained with conventional nine volt batteries.

As a variant of the invention, the power source can be a D.C. voltage source available in conventional automotive vehicles using a nine volt cigarette lighter convertor. Typically the cigarette lighter power source has a voltage of about twelve volts. It can be used for prolonged time periods without worry that it will run down or become ineffective.

Accordingly a treatment system powered from the automotive electrical power supply, e.g. the cigarette lighter outlet, can be used for treatments lasting more than a few minutes, e.g. three seven minute sessions per day for a one week time period.

Further features and advantages of the invention will be apparent from the attached drawings and description of a preferred embodiment of the invention.

DESCRIPTION OF THE PREFERRED EMBODIMENT

Figure 1:
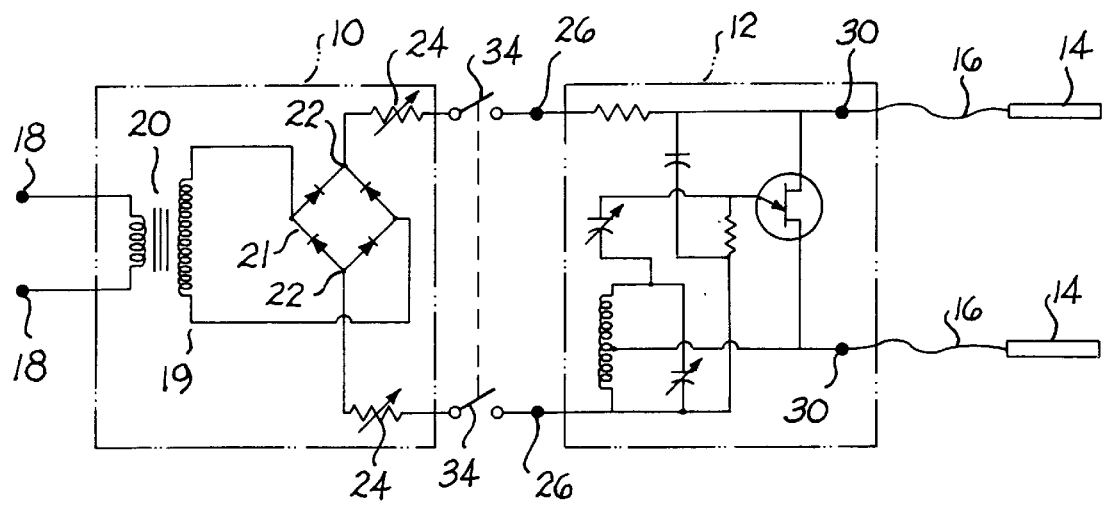
FIG. 1 is an electrical schematic diagram of an electrical circuit that can be used practicing the invention.

FIG. 1 of the drawings, shows an electrical apparatus (or circuit) designed for killing a variety of viruses, bacteria, parasites, toxins and harmful micro-organisms in the human body. The illustrated circuit comprises a D.C. voltage source 10, an oscillator circuit 12 powered by said D.C. voltage source, and two electrodes 14 connected to the oscillator output via flexible insulated conductors 16. The electrodes are adapted to be held in the hands of a person who is being treated, whereby the oscillating current generated by the oscillator passes through the person's body. The oscillating current is of sufficient magnitude to kill harmful viruses, bacteria and parasites that may be present in the person's body.

Voltage source 10 comprises a conventional household A.C. voltage outlet 18, and an A.C.-D.C. convertor 19 pluggable into the outlet. The convertor comprises a step down transformer 20 having lead wires pluggable into said outlet, and a diode bridge circuit 21 connected to the transformer secondary to provide a D.C. voltage across terminals 22 of the bridge circuit.

Variable (adjustable) resistances 24 are provided in the electrical circuit lines leading from terminals 22, to vary the D.C. voltage supplied to oscillator input terminals 26. Typically, the D.C. voltage across terminals 26 is about fifteen or twenty volts. Voltages higher than twenty volts are not recommended because of the potential health hazard posed by such higher voltages.

Oscillator circuit 12 is a Hartley oscillator that includes a unijunction transistor, a split inductance, and two manually adjustable capacitances, whereby the oscillator output terminals 30 provide an A.C. output current whose frequency varies between approximately 100 Khz and 900 Khz. Variation in the oscillator output frequency is achieved by manual adjustment of the capacitance values in the oscillator circuit. The peak value of the current at terminals 30 is determined by the resistance (impedance) values in the oscillator circuit. Typically the peak current is less than one ampere, preferably in the range of fifty milliamperes; the main consideration is human safety and limitations imposed by the oscillator circuitry.

Each electrode 14 preferably comprises a thin wall tubular copper member. Each tubular member has a preferred length of about 4' and a diameter of about 1°, and can be grasped in a person's hand without cramping the fingers or causing a loss of finger (hand) pressure on the electrode surface. The aim is to provide an electrically conductive electrode having a relatively large area contact with the person's palm and fingers whereby the oscillating current surges can effectively enter the person's body where harmful bacteria and micro-organisms may reside.

In use of the apparatus, convertor 19 is plugged into A.C. outlet 18, and manual switch 34 is closed to put oscillator circuit 12 into operation. The person grasps electrodes 14 in his/her hands (one electrode in each hand), so that the oscillating current generated at terminals 30 flows through lead wires 16 and electrodes 14 into the person's body.

Terminals 30 are located in the oscillator circuit so that the respective electrodes 14 are alternately exposed to the positive voltage peaks in the oscillating current. One electrode 14 will be at a positive peak voltage while the other electrode is at a negative peak voltage, and vice versa.

The illustrated oscillator circuitry provides a wave that alternates between positive and negative values. However, it is possible by using a half wave rectifier circuit at the oscillator output, to achieve a wave that oscillates between a zero value and a positive peak value. The shape of the wave is not considered to be important for purposes of the present invention.

The oscillation frequency preferably varies between 100 Khz and 900 KHz. This frequency range spans the spectrum of frequencies that kill a range of micro-organisms without damaging human blood or tissue.

During each treatment session the capacitances in the oscillation circuit may be arranged at different settings for selected time periods, such that different frequencies are selectively delivered to the human body. Assuming a total treatment time of eight minutes, the oscillation circuit can be set at each of eight different frequencies (in the specified frequency range) for one minute intervals. One frequency may be effective on one micro-organism, whereas a different frequency may be more effective on a different micro-organism. The cumulative effect is the destruction of a variety of different viruses, bacteria and micro-organisms.

A principal advantage of the illustrated circuit is that the oscillator is powered by a D.C. voltage source that comprises a conventional one hundred twenty volt A.C. voltage outlet 18. There is no danger that the power source will run down or become depleted, as might be the case if a conventional nine volt dry cell battery were to be used as the power source. The A.C. household voltage outlet (source) is also advantageous in that D.C. voltages higher than nine volts can be achieved at the oscillator input terminals 26.

Figure 2:
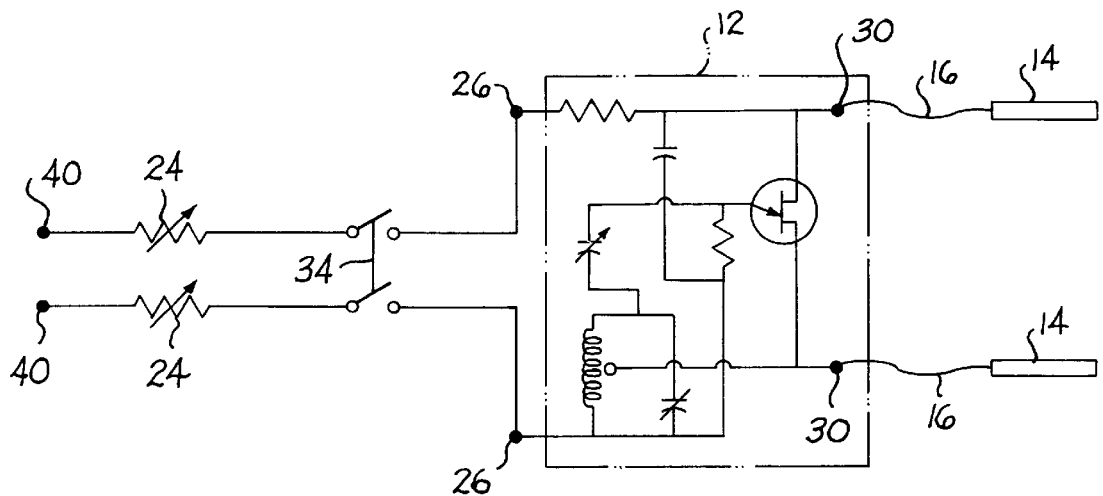
FIG. 2 shows another circuit that can be used according to the invention.

FIG. 2 shows a second circuit that can be employed in practicing the invention. The circuit is the same as that shown in FIG. 1 except that the D.C. power source for oscillator 12 takes the form of a nine volt cigarette lighter convertor 40. Typically such an outlet provides twelve volt D.C. power. Some larger vehicles provide twenty four volt D.C. power. In either case, the D.C. power provided by the vehicle wet cell battery is long lasting and at a relatively steady state, so that the D.C. voltage source can be used in practicing of the invention. There is no likelihood that the D.C. power source will run-down during the course of a treatment session.

The invention can use the A.C.-D.C. convertor of FIG. 1 or the D.C. power outlet 40 of FIG. 2. Either power source can be utilized to run the oscillator circuit 12 that supplies high frequency oscillating current to the electrodes 14. In either case the circuitry is adapted to kill a variety of viruses and micro-organisms in the person's blood.

Figure 3:
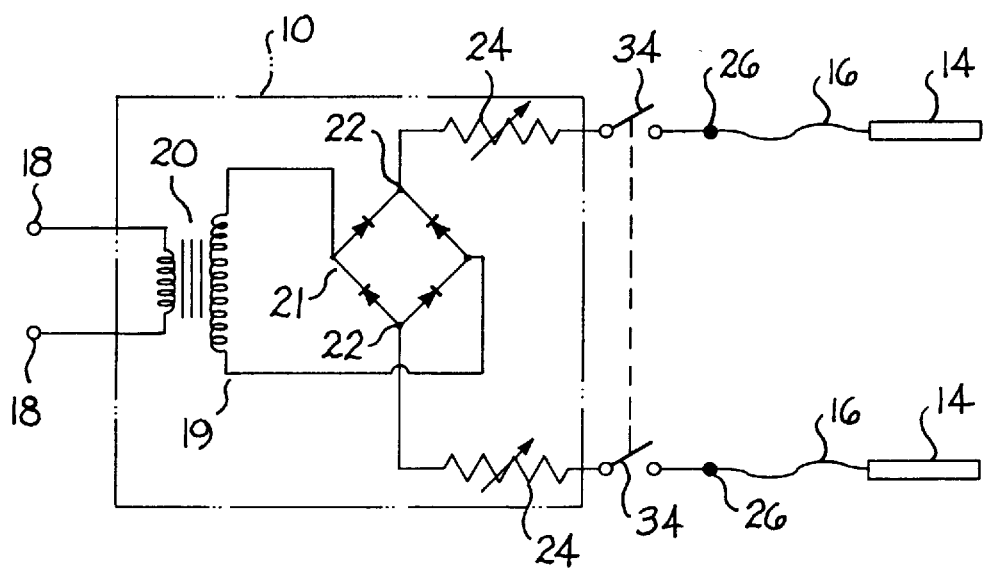
FIG. 3 shows another circuit illustrating a further embodiment of the invention.

FIG. 3 shows another embodiment of the invention in which the D.C. voltage source 10 is directly connected to the insulated conductors 16 through manual switches 34. In this case one of the electrodes is connected to the positive side of the convertor while the other electrode is connected to the negative side of the convertor. The user grasps the negative electrode and then taps the positive electrode after first wetting his hands. The reason is unclear but apparently the theory is placing your hands by a water faucet discharges the body's internal capacitors. When the user then grasps the terminals he will have a low resistance of about 10–15 KΩ. The resistance soon rises to 20 KΩ. The body's capacitors then come into play by tapping the positive terminal with a wet hand at a fairly high rate. Tapping the terminal stops and starts the voltage to the body's internal capacitors so they charge and discharge and the body does not build up a resistance to the electrical current. The faster the user taps the greater the frequency of recurring pulses and the lower the resistance becomes.

The drawings show specific circuits and features that can be used in practice of the invention. However, it will be appreciated that the invention can take various forms and configurations. For example, a source of solar power could be used for energizing the device.

Having described my invention, I claim:

1. An electrical apparatus for killing bacteria and microorganisms in the human body, comprising:

a D.C. voltage source;

an oscillator means powered by said D.C. voltage source;

electrode means (14, 16) powered by said oscillator means; and manual switch means (34, 34) connected between said D.C. voltage source and said oscillator means for turning said oscillator means on or off;

said D.C. voltage source comprising a household A.C. voltage outlet and an A.C.-D.C. converter pluggable into said outlet; said A.C.-D.C. converter comprising a step down transformer having an input and an output, a diode bridge circuit connected to the transformer output, and manually adjustable resistance means (24, 24) connected between said bridge circuit and said manual switch means for varying the D.C. voltage supplied to said oscillator means when said manual switch means is in the conductive state;

said oscillator means comprising a transistor means, a split inductance, and manually adjustable capacitance means in circuit with said transistor means and said inductance for varying the current frequency produced by said oscillator means; said oscillator means having two separate output terminals (30, 30) located so that a positive peak voltage is produced at one of said terminals while a negative peak voltage peak is being produced at the other terminal; and said electrode means comprising two separate electrodes (14, 14) adapted to be simultaneously held in a person's hands, and a flexible insulated lead (16) connecting each said electrode to a different one of the output terminals of said oscillator means, whereby voltage peaks of opposite polarity are simultaneously delivered to the person's body through said electrodes.

* * * * *